United States Patent
Jin et al.

(10) Patent No.: US 10,087,452 B2
(45) Date of Patent: Oct. 2, 2018

(54) METHOD FOR AGROBACTERIUM MEDIATED TRANSFORMATION OF CAMBIAL MERISTEMATIC PLANT CELLS TO PRODUCE RECOMBINANT PROTEIN

(71) Applicant: WELLKEY HOLDINGS LIMITED, Road Town Tortola (VG)

(72) Inventors: Young Woo Jin, Jeonju-si (KR); Eun Kyong Lee, Iksan-si (KR); Mi Ok Jang, Jeonju-si (KR); Bora Park, Daejeon (KR); Soo Ran Lee, Wanju-Gun (KR); Bo Rim Yang, Jeonju-si (KR); Il Suk Kim, Jeonju-si (KR); Il Seok Oh, Wanju-Gun (KR)

(73) Assignee: WELLKEY HOLDINGS LIMITED, Road Town Tortola (VG)

( * ) Notice: Subject to any disclaimer, the term of this patent is extended or adjusted under 35 U.S.C. 154(b) by 0 days.

(21) Appl. No.: 14/771,483

(22) PCT Filed: Feb. 28, 2014

(86) PCT No.: PCT/KR2014/001694
§ 371 (c)(1),
(2) Date: Aug. 28, 2015

(87) PCT Pub. No.: WO2014/133365
PCT Pub. Date: Sep. 4, 2014

(65) Prior Publication Data
US 2016/0010099 A1    Jan. 14, 2016

(30) Foreign Application Priority Data
Feb. 28, 2013   (KR) .................. 10-2013-0022404

(51) Int. Cl.
*C12N 15/82*   (2006.01)
*C12N 5/04*   (2006.01)

(52) U.S. Cl.
CPC ........... *C12N 15/8205* (2013.01); *C12N 5/04* (2013.01); *C12N 15/8257* (2013.01)

(58) Field of Classification Search
None
See application file for complete search history.

(56) References Cited

U.S. PATENT DOCUMENTS 8,053,238 B2 * 11/2011 Jin ........................ C12N 5/04
435/410

FOREIGN PATENT DOCUMENTS

| CN | 1460718 A | 12/2003 |
|---|---|---|
| CN | 1940066 A | 4/2007 |
| CN | 101195832 A | 6/2008 |
| CN | 101319206 A | 12/2008 |
| CN | 102459572 A | 5/2012 |
| CN | 102459573 A | 5/2012 |
| EP | 2436758 A2 | 4/2012 |
| JP | 2006-524506 A | 11/2006 |
| JP | 2012-504392 A | 2/2012 |
| JP | 2012-527890 A | 11/2012 |
| KR | 10-2007-0050207 A | 5/2007 |
| KR | 10-2011-0004922 A | 1/2011 |
| KR | 10-1064519 B1 | 9/2011 |
| KR | 10-2012-0052841 A | 5/2012 |
| KR | 10-2012-0128878 A | 11/2012 |
| WO | 2004/096978 A2 | 11/2004 |
| WO | 2009/038417 A2 | 3/2009 |
| WO | 2010/037208 A1 | 4/2010 |
| WO | 2010-137877 A | 12/2010 |
| WO | 2010/137918 A2 | 12/2010 |
| WO | 2012/052854 A2 | 4/2012 |

OTHER PUBLICATIONS

Schrammeijer et al. Meristem transformation of sunflower via Agrobacterium. (1990) Plant Cell Reports; vol. 9; pp. 55-60.*
Lee et al. Cultured cambial meristematic cells as a source of plant natural products. (2010) Nature Biotechnology; vol. 28; pp. 1213-1217.*
Kim et al. Direct transfer and expression of human GM-CSF in tobacco suspension cell using Agrobacterium-mediated transfer system. (2004) Plant Cell, Tissue and Organ Culture; vol. 78; pp. 133-138.*
Neumann et al., "Gene transfer into mouse lyoma cells by electroporation in high electric fields", EMBO J., 1982, vol. 1, No. 7, pp. 841-845.
International Search Report dated Jun. 8, 2014 of PCT/KR2014/001694 which is the parent application and its English translation—4 pages.
Yun et al., "Plant natural products: history, limitations and the potential of cambial meristematic cells", Biotechnology and Genetic Engineering Reviews, 2012, vol. 28, pp. 47-60.
Canadian Office Action dated Jun. 28, 2016 of corresponding Canadian Patent Application No. 2,902,808—5 pages.

(Continued)

*Primary Examiner* — Cathy Kingdon Worley
(74) *Attorney, Agent, or Firm* — Hultquist, PLLC; Steven J. Hultquist

(57) ABSTRACT

Plant cells express a target protein, a production method thereof, and a method of producing a target protein using the same are disclosed. The plant cells have introduced therein a recombinant vector containing gene(s) encoding a target protein, and the plant cells include plant cambial meristematic cells (CMC) or callus. The cambial meristematic cells (CMCs) are a cell line containing innately undifferentiated cells isolated from a plant, wherein the cell line is a cell line isolated from the cambial tissue of the plant and has meristematic continuity without going through dedifferentiation into callus. A system of expressing a target protein using the recombinant plant cells according to the present invention can overcome the problems of conventional plant cell culture. In addition, it shows significantly high transformation efficiency, and thus can produce large amounts of target proteins, including biopharmaceutical proteins.

5 Claims, 12 Drawing Sheets
(10 of 12 Drawing Sheet(s) Filed in Color)

(56) References Cited

OTHER PUBLICATIONS

Chinese Office Action dated May 31, 2016 of corresponding Chinese Patent Application No. 201480019682.9—24 pages.
Japanese Office Action dated Aug. 4, 2016 of corresponding Japanese Patent Application No. 2015-560106—3 pages.
Extended European Search Report dated Sep. 19, 2016 of corresponding European Patent Application No. 14756381.1—6 pages.
Rodriguez et al., "The same treatment for transgenic shoot regeneration elicits the opposite effect in mature explants from two closely related sweet orange (Citrus sinensis (L.) Osb.) genotypes", Plant Cell Tiss Organ Cult, 2008, vol. 93, pp. 97-106.

* cited by examiner

US 10,087,452 B2

METHOD FOR AGROBACTERIUM MEDIATED TRANSFORMATION OF CAMBIAL MERISTEMATIC PLANT CELLS TO PRODUCE RECOMBINANT PROTEIN

TECHNICAL FIELD

The present invention relates to plant cells that express a target protein, a production method thereof, and a method of producing a target protein using the same. Moreover, the present invention relates to plant cells which have been introduced a vector containing gene(s) that encodes the target protein and thus expresses the target protein, a production method thereof, and a method of mass production of a target protein by the plant cells.

BACKGROUND ART

As used herein, the term "biopharmaceuticals" refers to drugs produced from biological materials. In a broader sense, the term may refer to drugs produced based on bioengineering technologies, including genetic recombination, cell fusion and cell culture, which are advanced biotechnologies. Such biopharmaceuticals are classified into protein drugs, therapeutic antibodies, vaccine, gene therapy agents and cell therapy agents.

Recently, most recombinant proteins have been produced either using eukaryotic host cells such as animal cells or insect cells, or by microorganisms such as yeast or bacteria. However, the culture of such animal cells has shortcomings in that media are costly, the possibility of contamination with viruses capable of infecting humans is high, and a separate purification process for removing bovine serum-derived proteins that may be introduced is required (Huang and McDonald 2009).

For this reason, plant cell culture has recently received attention as an alternative system for production of recombinant proteins. Plant cells are regarded as a safe production system, because these plant cells are not infected with a virus or pathogen of animal origin and there is no possibility of incorporation of a material of animal origin.

However, plant cell culture shows relatively low protein expression levels and slow growth rates compared to the culture of other host cells, including animal cells. Thus, for the commercialization of plant-derived biopharmaceuticals, the development of new systems of producing recombinant proteins by culture of new plant cells has been requested.

The information disclosed in the Background Art section is only for the enhancement of understanding of the background of the present invention, and therefore may not contain information that forms a prior art that would already be known to a person of ordinary skill in the art.

DISCLOSURE OF INVENTION

It is an object of the present invention to provide a method for producing a target protein, which has excellent productivity enabling mass production.

To achieve the above object, the present invention provides plant cells for expression of a target protein, wherein the plant cells comprising a recombinant vector comprising gene(s) encoding the target protein introduced therein, wherein the plant cells comprising cambial meristematic cells (CMCs) or callus, wherein the cambial meristematic cells (CMCs) are a type of plant derived cell line comprising innately undifferentiated cells isolated from a plant, and wherein the cell line is isolated from the cambial tissue of the plant and has meristematic continuity without going through dedifferentiation into callus.

The present invention also provides a method for producing plant cells for expression of a target protein, the method comprising a step of transfecting or transforming a population of plant cells including cambial meristematic cells (CMCs) or callus with gene(s) encoding the target protein, by co-culturing the population of plant cells including cambial meristematic cells (CMCs) or callus with an Agrobacteriua containing a vector comprising the gene encoding the target protein added thereto, wherein the cambial meristematic cells (CMCs) are a cell line containing innately undifferentiated cells isolated from a plant, the cell line being isolated from the cambial tissue of the plant and having meristematic continuity without going through dedifferentiation into callus.

The present invention also provides a method of producing a target protein by plant cells for expression of the target protein, the method comprising the steps of: (a) stably transforming a population of plant cells including cambial meristematic cells (CMCs) or callus with gene(s) encoding the target protein or transiently expressing the gene(s) encoding the target protein, by co-culturing the population of plant cells including cambial meristematic cells (CMCs) or callus with an Agrobacteria containing a vector comprising the gene encoding the target protein added thereto, wherein the cambial meristematic cells (CMCs) are a cell line containing innately undifferentiated cells isolated from a plant, the cell line being isolated from the cambial tissue of the plant and having meristematic continuity without going through dedifferentiation into callus; and (b) recovering the target protein expressed in the culture of plant cells, in which the Agrobacteria are infected by the co-culture.

The present invention also provides a method of producing a target protein from a transgenic plant for expression of the target protein, the method comprising the steps of:

(a) growing a plant transformed with gene(s) encoding the target protein;

(b) isolating transgenic cambial meristematic cells (TCMCs) from the transgenic plant;

(c) culturing the isolated transgenic cambial meristematic cells (TCMCs) in a medium; and (d) recovering the target protein expressed in the cultured transgenic cambial meristematic cells (TCMCs).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF EMBODIMENTS

Figure 1:
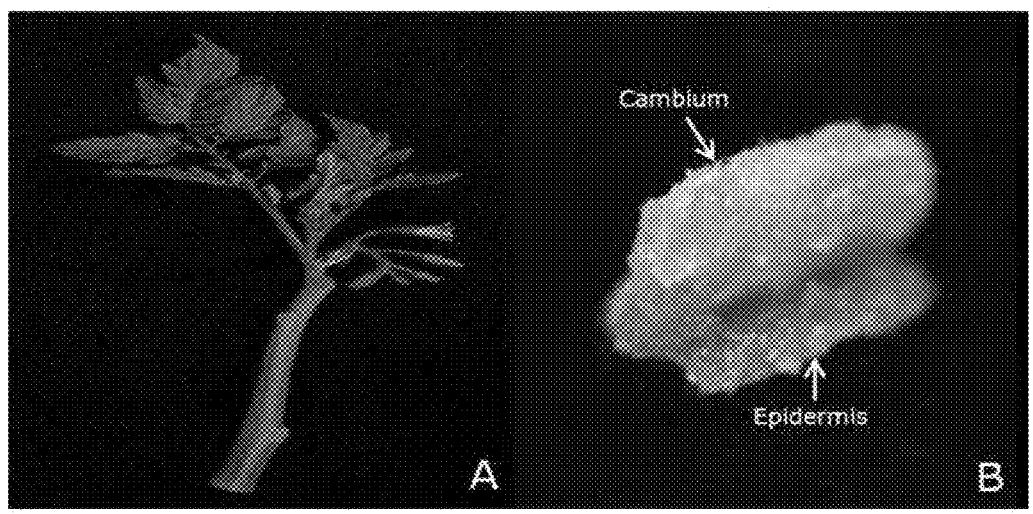
FIG. 1 shows a set of photographs, wherein A of FIG. 1 is a photograph of a material plant (tomato stem), and B of FIG. 1 is a photograph showing that cambial meristematic cells (CMCs) were induced and started to be separated from a callus layer derived from other tissue.

Unless defined otherwise, all technical and scientific terms used herein have the same meaning as commonly understood by one of ordinary skill in the art to which the invention pertains. Generally, the nomenclature used herein is well known and are commonly employed in the art.

Plant cells for expression of a target protein have introduced therein a recombinant vector containing gene(s) encoding the target protein and the plant cells include cambial meristematic cells (CMCs) or callus.

In one embodiment, the plant cells may be transgenic cambial meristematic cells (TCMCs) having introduced therein a recombinant vector containing gene(s) encoding a target protein.

The present inventors have found that the introduction of a gene encoding a target protein into cambial meristematic cells (CMCs) makes it possible to overcome problems caused by slow growth rates and low protein expression levels, which arise from callus culture according to the prior art. In addition, the present inventors have found that, if a recombinant protein is produced by transforming plant cambial meristematic cells (CMCs), the transformation efficiency of the cells can be significantly increased compared to that of previously known plant cells so that the significantly increased production of a recombinant protein is possible by the application of a technique for transient expression of a target protein, and stable transformation can also be established.

Herein, the cambial meristematic cells (CMCs) are a cell line containing innately undifferentiated cells isolated from a plant. The cell line is isolated from the cambial tissue of the plant and has meristematic continuity without going through dedifferentiation into callus.

In the present invention, callus is an amorphous cell mass that is formed through the dedifferentiation of differentiated tissue by injury. After dedifferentiation, callus loses its original characteristics and is present in an undifferentiated state. Plant cambial meristematic cells (CMCs) that are used in the present invention differ from callus in that they are maintained in an innately undifferentiated state without going through dedifferentiation.

Some of the present inventors first isolated plant cambial meristematic cells (CMCs), which are innately undifferentiated cells different from dedifferentiated callus, from the plant cambium (KR 10-1064519 B1). Such plant cambial meristematic cells can be isolated by a method comprising the steps of: (a) collecting a cambium-containing tissue from a plant; (b) culturing the collected cambium-containing tissue in a medium; and (c) isolating cambial cells, which include neither portions other than the cambium nor callus derived from portions other than the cambium, from the cultured cambium-containing tissue. Herein, the cambium-containing tissue in step (a) may be sterilized.

As used herein, the term "vector" means a DNA construct containing a DNA sequence operably linked to a suitable control sequence capable of effecting the expression of the DNA in a suitable host. The vector may be a plasmid, a phage particle, or simply a potential genomic insert. Once incorporated into a suitable host, the vector may replicate and function independently of the host genome, or may in some instances, integrate into the genome itself. In the present specification, "plasmid" and "vector" are sometimes used interchangeably, as the plasmid is the most commonly used form of vector.

For the purpose of the present invention, the plasmid vector is preferably used. A typical plasmid vector which can be used for this purpose contains: (a) a replication origin by which replication occurs efficiently such that several hundred plasmid vectors per host cell are created; (b) an antibiotic-resistant gene by which host cells transformed with the plasmid vector can be selected; and (c) restriction enzyme sites into which foreign DNA fragments can be inserted. Even if suitable restriction enzyme sites are not present in the vector, the use of a conventional synthetic oligonucleotide adaptor or linker enables the easy ligation between the vector and the foreign DNA fragments. After ligation, the vector should be transformed into suitable host cells. The transformation can be easily achieved by the calcium chloride method or electroporation (Neumann, et al., EMBO J., 1:841, 1982).

As the vector which is used for the overexpression of a gene according to the present invention, an expression vector known in the art may be used. In the present invention, a binary vector used for transformation of a plant was used.

As is well known in the art, in order to increase the expression level of an introduced gene in a host cell, a corresponding gene should be operably linked to transcription and translation expression regulatory sequences. Preferably, the expression regulatory sequences and the corresponding gene are included in one expression vector together with a bacterial selection marker and a replication origin. A recombinant vector preferably further includes an expression marker which is useful in a plant cell.

The transgenic cambial meristematic cells (TCMCs) with the aforementioned expression vector constitute another aspect of the present invention. As used herein, the term "transformation" means that DNA can be replicated as a factor outside of chromosome or by means of completion of the entire chromosome by introducing DNA into a host. Meanwhile, as used herein, the term "transfection" means that DNA is introduced into host cells so that it can be replicated in the host cells.

Of course, it should be understood that all vectors and expression regulatory sequences do not equally function to express DNA sequences in a cambial meristematic cell (CMC) system according to the present invention. However, one skilled in the art may appropriately select from among various vectors and expression regulatory sequences without either departing from the scope of the present invention or bearing excessive experimental burden. Specifically, the copy number of the vector, the ability of regulating the copy number and the expression of other protein encoded by the corresponding vector (e.g., the expression of an antibiotic marker) should also be considered.

As described above, the gene(s) encoding the target protein can be transiently expressed in plant cambial meristematic cells (CMCs) or stably transformed into the cells, by use of a vector.

In addition, not only the gene(s) encoding the target protein is introduced into plant cambial meristematic cells (CMCs) and transiently expressed therein, but also the gene(s) encoding the target protein can be introduced into the genome of the plant cambial meristematic cells (CMCs) so that it can be present on the chromosome and can be stably transformed into the cells. It will be obvious to those skilled in the art to which the present invention pertains that the insertion of the target protein-encoding gene(s) into the genome (chromosome) of plant cambial meristematic cells (CMCs) has the same effect as that of the introduction of the recombinant vector into plant cambial meristematic cells (CMCs) as described above.

Therefore, in another aspect, the present invention is directed to transgenic cambial meristematic cells (TCMCs) for expression of a target protein, which comprise a target protein-encoding gene(s) inserted into the chromosome of cambial meristematic cells (CMCs).

In the present invention, the introduction of a vector comprising the target protein-encoding gene(s) or the insertion of the target protein-encoding gene(s) into the chromosome of cambial meristematic cells (CMCs) may be performed by adding an *Agrobacteria* containing a vector comprising gene(s) encoding the target protein to a population of plant cells including cambial meristematic cells (CMCs) or callus and co-culturing the *Agrobacteria* with the plant cells.

In an embodiment, the co-culture may be performed under dark conditions. The co-culture may be performed by culturing plant cells including plant cambial meristematic cells (CMCs) or callus with culture of *Agrobacteria* containing a vector comprising the target protein-encoding gene(s) with shaking, and may be followed by a stationary culture.

The term "static culture" as used herein means a method of culturing cells in a container with static status without shaking a culture medium, and may be used interchangeably with a method of sedimenting cells without shaking.

The static culture may be single performed static culture or in an intermittently performed static culture. When the static culture is performed once (single performed static culture), the plant cells and the culture of *Agrobacteria* may, for example, be co-cultured with shaking, subjected to static culture, and then to agitated culture. When the static culture is performed in an intermittent fashion (intermittently performed static culture), a process that comprises repeated several times to several tens of times of culturing as follows: co-culturing the plant cells and the culture of *Agrobacteria* with shaking, subjecting the plant cells and the *Agrobacteria* culture to static culture, and then co-culturing the plant cells and the *Agrobacteria* culture with shaking again.

Specifically, the culture process may be performed by co-culturing the plant cells and culture of *Agrobacteria* containing the vector comprising the target protein-encoding gene(s) with shaking for 1 minute to 48 hours, subjecting the plant cells and the culture of *Agrobacteria* to static culture for 1 minute to 96 hours, and then subjecting the culture to an agitated culture for 1-10 days.

The *Agrobacteria* that are added for co-culture may have an $OD_{600}$ of 0.00001-2.0. If the $OD_{600}$ of the *Agrobacteria* is too low, there will be a problem in that transfection rate for transient expression decreases, and if the $OD_{600}$ of the *Agrobacteria* are too high, there will be a problem in that the viability of host cells decreases rapidly. Thus, *Agrobacteria* having an $OD_{600}$ in the above-defined range is preferably added and co-cultured.

The *Agrobacteria* that are used in the present invention may be *Agrobacteria* that are generally used for plant transformation. For example, the *Agrobacteria* may be *Agrobacterium tumefaciens* or *Agrobacterium rhizogenes*.

As described above, the target protein can be produced by culturing the transgenic cambial meristematic cells (TCMCs) to express the target protein therein and recovering the expressed target protein.

In another embodiment, the transgenic cambial meristematic cells (TCMCs) may also be isolated from a transgenic plant with the gene(s) encoding the target protein.

In the present invention, a tobacco plant was stably transformed with a target protein-encoding gene(s) and grown in a flowerpot. As a result, it was found that the expression level of the target protein-encoding gene(s) in the cambium was higher than those in other tissues.

The target protein that is used in the present invention may, for example, be one or more proteins selected from the group consisting of antigens, antibodies, antibody fragments, structural proteins, regulatory proteins, transcriptional factor, toxin proteins, hormones, hormone analogues, cytokines, enzymes, enzyme inhibitors, transport proteins, receptors, receptor fragments, host defense inducers, storage proteins, movement proteins, exploitive proteins and reporter proteins, but is not limited thereto.

In an example of the present invention, meristematic cells were isolated from the cambium of each of tomato, carrot, taxus and wild ginseng plants, and then transformed with *Agrobacteria* containing green fluorescent protein (GFP) gene, after which the expression of GFP in the cells was analyzed. As a result, it was shown that transient expression of GFP or stable transformation with GFP was successful. In addition, it could be seen that, even when the cells were subcultured at intervals of 2 weeks, the cells were stably proliferated and the target protein GFP was also stably expressed in the cells.

In an example of the present invention, as a result of transiently expressing a gene encoding target protein in the *Agrobacteria* in the tomato cambial meristematic cells (CMCs), it could be seen that, at 1-9 days of co-culture, and most preferably 5 days of co-culture, 90% or more of viable cells were infected with the *Agrobacteria* and expressed GFP. During the co-culture period, the tomato cambial meristematic cells (CMCs) showed a decrease in viability of less than 10%, and the rigidity of the cell wall was maintained intact. It was previously reported that transformation at the cell culture level has efficiency as low as 10% or lower, but it could be seen that the application of plant cambial meristematic cells (CMCs) according to the present invention showed a high transformation efficiency of 90% or higher.

This high transformation efficiency indicates that a recombinant protein can be produced at commercial levels by transient expression. This production is possible without having to perform a separate selection process, and thus a selection marker cassette may be eliminated from a vector. In addition, only a target protein can be expressed with high transformation efficiency, and thus the present invention is significantly advantageous in terms of efficiency.

Meanwhile, tomato callus was cultured under the same conditions as described above, and as a result, the tomato callus showed a low transformation efficiency of 26.4%, unlike the plant meristematic cells of the present invention. However, it was found that this value was at least two times higher than 10%, which is the previously reported callus transformation efficiency. This indicates that the method for producing a recombinant protein according to the present invention can be applied not only to plant cambial meristematic cells (CMCs), but also to callus.

In another aspect, the present invention is directed to a method of producing a target protein by plant cells for expression of the target protein, the method comprising the steps of:

(a) stably transforming a population of plant cells including cambial meristematic cells (CMCs) or callus with gene(s) encoding the target protein or transiently expressing the gene(s) encoding the target protein, by co-culturing the population of plant cells including cambial meristematic cells (CMCs) or callus with *Agrobacteria* containing a vector comprising the gene(s) encoding the target protein added thereto, wherein the cambial meristematic cells (CMCs) are a cell line containing innately undifferentiated cells isolated from a plant, the cell line being isolated from the cambial tissue of the plant and having meristematic continuity without going through dedifferentiation into callus; and (b) recovering the target protein expressed in the culture of plant cells, in which the *Agrobacteria* are infected by the co-culture.

In another aspect, the present invention is directed to a method of producing a target protein by a transgenic plant with gene(s) encoding the target protein, the method comprising the steps of:

(a) growing a transgenic plant with gene(s) encoding the target protein;

(b) isolating transgenic cambial meristematic cells (TC-MCs) from the transgenic plant;

(c) culturing the isolated transgenic cambial meristematic cells (TCMCs) in a medium; and (d) recovering the target protein expressed in the cultured transgenic cambial meristematic cells (TCMCs).

EXAMPLES

Hereinafter, the present invention will be described in further detail with reference to examples. It will be obvious to a person having ordinary skill in the art that these examples are illustrative purposes only and are not to be construed to limit or change the scope of the present invention.

Example 1

Production, Proliferation and Characterization of Cambial Meristematic Cells (CMCs) of Plants of the Family Solanaceae 1-1: Preparation of Tomato Plant Material To isolate cambial meristematic cells (CMCs) from tomato (*Lycopericum esculentum*, Sejong Seed Co., Ltd., Korea), a member of the genus *Lycopersicon* of the family Solanaceae, the stem and twigs (A of FIG. 1) were collected from tomato, and then immediately soaked in 100 mg/L of the antioxidant ascorbic acid (L-ascorbic acid, DUCHEFA, The Netherlands), after which they were transported and stored.

Then, the plant was pretreated with a mixed solution of 0.1% benomyl (Dongbu Hannong Chemical, Korea), 0.1% daconil (Dongbu Hannong Chemical, Korea), 0.1% streptomycin sulphate (DUCHEFA, The Netherlands) and 0.01% cefotaxime sodium (DUCHEFA, The Netherlands) for 10 minutes, and then washed with tap water for 5 minutes to remove phenolic compounds and the remaining chemicals. Next, the plant was surface-sterilized in 70% ethanol (DC Chemical, Korea) for 1 min, 1.5% hydrogen peroxide (LG Chemical, Korea) for 3 min, 0.5% CLOROX solution for 5 min and 0.1% CLOROX solution for 5 min, and then washed 3-4 times with water.

1-2: Preparation of Cambium-containing Explant from Stem of Tomato Plant and Separation of Tissue The stem sterilized in Example 1-1 was cut, and the phloem, cortex and epidermis tissues containing a cambium having an excellent ability to divide were peeled off from the xylem.

1-3: Induction of Tomato Cambium-derived Stem Cells

The cambium-containing explant prepared in Example 1-2 above was planted and cultured in the cambial meristematic cell (CMC) induction medium (medium 1) shown in Table 1 below.

TABLE 1

Cambial meristematic cell (CMC) induction medium (medium 1)

| | Composition | Contents(mg/L) |
|---|---|---|
| Inorganic salts | $KNO_3$ | 2500 |
| | $(NH_4)_2SO_4$ | 134 |
| | $MgSO_4 7H_2O$ | 121.56 |
| | $MnSO_4 4H_2O$ | 10 |
| | $ZnSO_4 7H_2O$ | 2 |
| | $CuSO_4 5H_2O$ | 0.025 |
| | $CaCl_2 2H_2O$ | 113.23 |
| | KI | 0.75 |
| | $CoCl_2 6H_2O$ | 0.025 |
| | $NaH_2PO_4 H_2O$ | 130.44 |
| | $H_3BO_3$ | 3 |
| | $Na_2MoO_4 2H_2O$ | 0.25 |
| | FeNaEDTA | 36.7 |
| Vitamin | Myo-inositol | 200 |
| | Thiamine-HCl | 20 |
| | Nicotinic acid | 2 |
| | Pyridoxine-HCl | 2 |
| | L-ascorbic acid | 50 |
| | Citric acid | 75 |
| Amino acid | L-aspartic acid | 133 |
| | L-arginine | 175 |
| | Glycine | 75 |
| | Proline | 115 |
| Hormone | α-Naphtalene acetic acid | 1 |
| Sucrose | | 10,000 |
| Activated charcoal | | 100 |
| Gelrite | | 2,000 |

The growth regulator auxin such as NAA, IAA, IBA, 2,4-D or picloram may be added to the medium at a concentration of 0.5-5 mg/L. In this Example, NAA was added at a concentration of 1 mg/L. The culture was carried out in a dark room controlled at 25±1 ° C.

At 7-10 days of initial culture, the division of cells from the cambium was visually observed, and after 3 weeks (21 days) of culture, an amorphous callus formed by dedifferentiation started to be induced from the layer composed of phloem, cortex and epidermis. After 30 days of culture, the tissue started to be separated into the cultured cambium layer and the upper layer containing phloem, which is an amorphous callus layer (B of FIG. 1). After the tissue has been naturally completely separated into the two layers, only the cambium portion was separated and cultured. After the tissue has been separated, the white and soft portion thereof having good growth rate was subcultured in the same fresh medium as induction medium at intervals of 14 days.

The tomato cambial meristematic cells were stably maintained without variations in their growth rates, growth patterns and aggregation degrees when they were cultured for a long period, suggesting that they would be cultured in a large scale. However, callus derived from the tomato stem showed variation in their growth pattern and growth rate and a high degree of aggregation when they were cultured for a long period of time. Thus, the callus cells tuned brown, were necrotized and could not be stably cultured in a large scale.

1-4: Culture of Tomato Callus

Tomato callus (PC10623) purchased from the Biological Resource Center (Korea) was subcultured at intervals of 3 weeks.

1-5: Proliferation and Characterization of Cambial Meristematic Cells (CMCs) of Plants of the Family Solanaceae The tomato cambial meristematic cells (CMCs) isolated in Example 1-3 above were placed in a flask containing the liquid medium shown in Table 2 below. Then, the cells in the flask were cultured in a rotating shaker under dark conditions at 100 rpm at 25±1° C. For continuous culture, the tomato cambial meristematic cells (CMCs) cultured for proliferation were suspension-cultured at a cell-to-medium volume ratio of 1:10 for 7 days.

TABLE 2

Suspension medium (medium 3)

| | Composition | Contents(mg/L) |
|---|---|---|
| Inorganic salts | $Ca(NO_3)_2$ | 471.26 |
| | $NH_4NO_3$ | 400 |
| | $MgSO_4 7H_2O$ | 180.54 |
| | $MnSO_4 4H_2O$ | 22.3 |
| | $ZnSO_4 7H_2O$ | 8.6 |
| | $CuSO_4 5H_2O$ | 0.25 |
| | $CaCl_2 2H_2O$ | 72.5 |
| | $K_2SO_4$ | 990 |
| | $Na_2MoO_4 2H_2O$ | 0.25 |
| | $H_3BO_3$ | 6.2 |
| | $KH_2PO_4$ | 170 |
| | FeNaEDTA | 36.7 |
| Vitamin | Myo-inositol | 200 |
| | Thiamine-HCl | 20 |
| | Nicotinic acid | 2 |
| | Pyridoxine-HCl | 2 |
| | L-ascorbic acid | 50 |
| | Citric acid | 75 |
| Amino acid | L-aspartic acid | 133 |
| | L-arginine | 175 |
| | Glycine | 75 |
| | Proline | 115 |
| Hormone | α-Naphtalene acetic acid | 1 |
| Sucrose | | 30,000 |

Tomato callus (PC10623) was also seeded at the same ratio as described above, and the liquid medium used for culture of the tomato callus is shown in Table 3 below.

TABLE 3

Suspension medium (medium 4)

| | Composition | Contents(/L) |
|---|---|---|
| Inorganic salts | $KNO_3$ | 2,500 |
| | $(NH_4)SO_2$ | 134 |
| | $MgSO_4 7H_2O$ | 250 |
| | $MnSO_4 4H_2O$ | 10 |
| | $ZnSO_4 7H_2O$ | 2 |
| | $CuSO_4 5H_2O$ | 0.025 |
| | $CaCl_2 2H_2O$ | 150 |
| | $NH_4H_2PO_4$ | 150 |
| | $NaH_2PO_4$ | 150 |
| | $H_3BO_3$ | 3 |
| | KCl | 300 |
| | KI | 0.75 |
| | $CoCl_2 6H_2O$ | 0.025 |
| | $Na_2MoO_4 2H_2O$ | 0.25 |
| | $FeSO_4 7H_2O$ | 27.85 |
| | $Na_2$-EDTA | 37.25 |
| Vitamin | Myo-inositol | 100 |
| | Thiamine-HCl | 10 |
| | Nicotinic acid | 1 |
| | Pyridoxine-HCl | 1 |
| Hormone | α-Naphtalene acetic acid | 1 |
| | Kinetin | 0.1 |
| Sucrose | | 20,000 |

Figure 2:
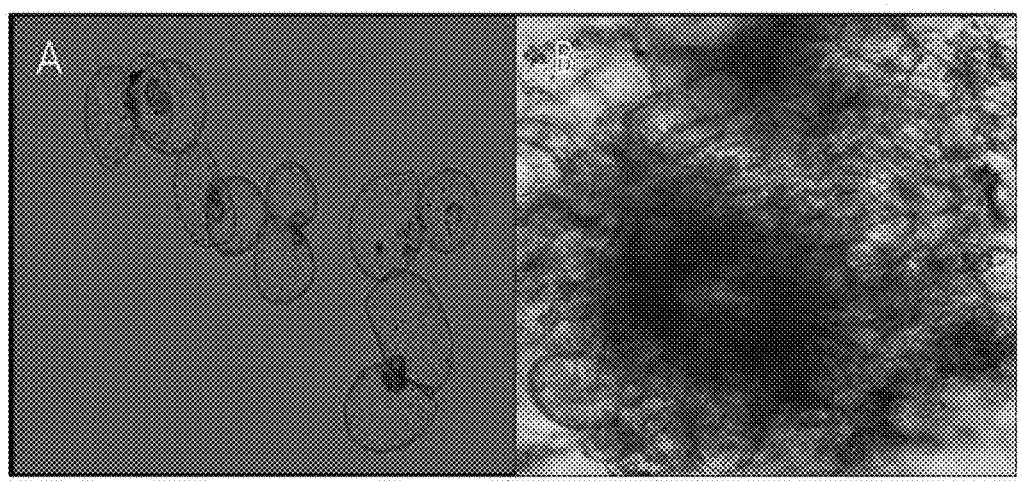
FIG. 2 is a set of micrographs showing the results of observing the extent of cell aggregation in tomato cambial meristematic cells (CMCs; A of FIG. 2) according to the present invention and tomato callus (B of FIG. 2).
Figure 3:
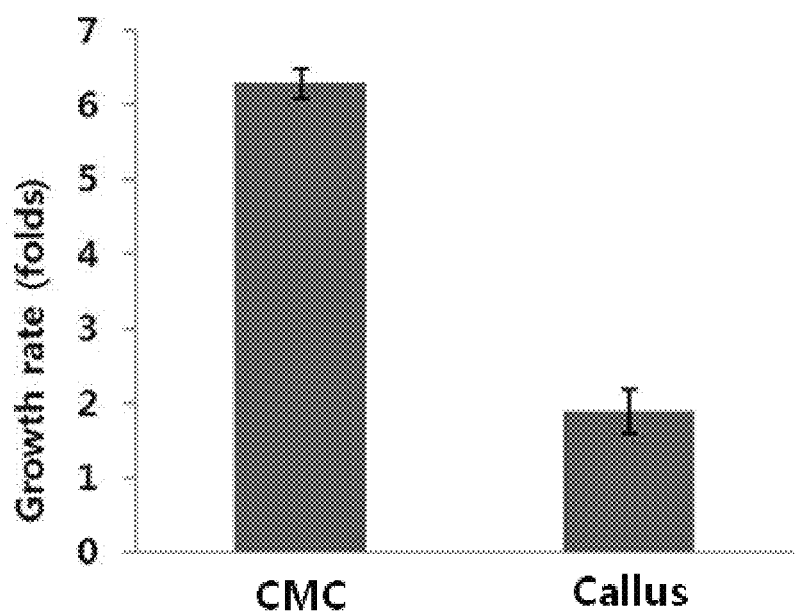
FIG. 3 is a graph showing the growth rate of each of tomato cambial meristematic cells (CMCs) according to the present invention and tomato callus.

The degree of aggregation of the cells was observed with biological microscope CX31 (Olympus, Japan). As a result, as shown in A of FIG. 2, it was observed that the cambial meristematic cells (CMCs) according to the present invention included a large number of single cells during suspension culture, and some of the cells were present as cell aggregates having a very small size. Specifically, when the cambial meristematic cells (CMCs) according to the present invention were cultured, the maximum size of the cell aggregates was only 500 µm. On the contrary, when the tomato callus (PC10623) was observed, the callus cells were highly aggregated as shown in B of FIG. 2, and the maximum size of the cell aggregates was 10 mm. In addition, the cambial meristematic cells (CMCs) according to the present invention and the cells of the callus (PC10623) were sampled after the proliferative culture, but before subculture, and the cell viability (%) of the samples were calculated using a 2% Evan's blue staining (5 min) method. As a result, as shown in Table 4, the cambial meristematic cells (CMCs) according to the present invention showed a viability of 96.33%, whereas the callus cells showed a viability of only 65.2%.

TABLE 4

Comparison of aggregate size and survival rate

| Cell lines | Aggregate size (µm) (Maximum size) | Survival rate (%) |
| --- | --- | --- |
| Cambial meristematic cells(CMC) | 500 | 96.33 |
| Callus | 10000 | 65.2 |

Example 2

Preparation of Cambial Meristematic Cells (CMCs) from Plant Storage Root 2-1: Preparation of Wild Ginseng Cambial Meristematic Cells (CMCs)

Smooth wild ginseng having no defect was selected, and fine roots were completely removed from the selected wild ginseng. Next, the remaining tissue was surface-sterilized in two steps. To prevent the browning of the sterilized tissue, the sterilized main root was placed in the antioxidant-containing browning inhibition medium (BIM) shown in Table 5 below, and was shake-cultured for about 30 minutes to 1 hour, after which it was placed on sterilized filter paper to remove moisture.

TABLE 5

BIM components and their concentrations

| Components | Concentrations |
| --- | --- |
| McCown WPM salt | ¼ strength |
| Sucrose | 1% (w/v) |
| PVP(polyvinyl pyrrolidone) | 0.5% (w/v) |
| Ascorbic acid | 100 mg/L |
| Citric acid | 150 mg/L | calibrated to pH 5.8

After completion of the sterilization process, in order to prevent the browning of the material, the material was cut to a size of 0.5-0.7 cm (W)×0.5-0.7 cm (L)×0.2-0.5 mm (H) in the antioxidant-containing cutting solution (CS) shown in Table 6 below so that it would include a cambium portion having an excellent ability to divide.

TABLE 6

Cutting solution (CS)

| Components | Concentrations |
| --- | --- |
| PVP(Polyvinyl pyrrolidone) | 0.5% (w/v) |
| Ascorbic acid | 100 mg/L |
| Citric acid | 150 mg/L |

To induce only the cambium in the prepared explant, the explant was placed in a flask containing a solution of 1M sucrose (Duchefa, Netherlands) and was treated with osmotic stress for 16-24 hours in a cold state. Then, the explant was treated in 0.05M sucrose solution for 5 min and in 0.1M sucrose solution for 5 min, thereby removing the stress caused by the high-concentration sucrose. The explant from which the osmotic stress has been removed was placed on a preinoculation medium (medium 6) having filter paper laid thereon to remove moisture.

TABLE 7

Composition of preinoculation medium (medium 6)

| Composition | | mM | mg/L |
| --- | --- | --- | --- |
| Macroelements | $Ca(NO_3)_2$ | 2.35 | 471.26 |
| | $NH_4NO_3$ | 5 | 400 |
| | $MgSO_4 \cdot 7H_2O$ | 1.5 | 180.54 |
| | $K_2SO_4$ | 5.68 | 990 |
| | $CaCl_2\ 2H_2O$ | 0.65 | 72.5 |
| | $KH_2PO_4$ | 1.25 | 170 |

| Composition | | µM | mg/L |
| --- | --- | --- | --- |
| Microelements | $MnSO_4 \cdot 4H_2O$ | 131.94 | 22.3 |
| | $ZnSO_4 \cdot 7H_2O$ | 29.91 | 8.6 |
| | $Na_2MoO_4 \cdot 2H_2O$ | 1.03 | 0.25 |
| | $H_3BO_3$ | 100.27 | 6.2 |
| | $CuSO_4 5H_2O$ | 1.0 | 0.25 |
| | FeNa-EDTA | 100 | 36.7 |
| Vitamin | Glycine | 26.64 | 2.0 |
| | myo-Inositol | 554.94 | 100 |
| | Nicotinic acid | 4.06 | 0.5 |
| | Pyridoxine-HCl | 2.43 | 0.5 |
| | Thiamine-HCl | 2.96 | 1.0 |

In order to induce wild ginseng cambial meristematic cells (CMCs), the explant treated with osmotic stress was placed on a cell line induction medium (medium 7). The medium used to induce cambial meristematic cells (CMCs) is shown in Table 8 below.

TABLE 8

Composition for medium (medium 8) for inducing cambial meristematic cells (CMCs)

| Composition and conditions | Concentrations and conditions |
| --- | --- |
| Salt | Full strength WPM |
| Sucrose | 3% (w/v) |
| IAA(Indole-3-acetic acid) | 1 mg/L |
| pH | 5.8 |
| Gelrite | 0.3% (w/v) |
| Ascorbic acid | 100 mg/L |
| Citric acid | 150 mg/L |

In the explant placed on the cell line induction medium (medium 7) after osmotic treatment and removal as described above, cambial meristematic cells (CMCs) were induced specifically in the cambium without being induced in other tissues.

After tissues other than the cambium were necrotized by culture in medium 7, the explant was cultured in medium 3-1 to proliferate only cambial cells.

TABLE 9

Medium 3-1

| | Composition | Contents (mg/L) |
|---|---|---|
| Inorganic salts | $KNO_3$ | 1900 |
| | $(NH_4)_2SO_4$ | 1650 |
| | $MgSO_4 7H_2O$ | 180.54 |
| | $MnSO_4 4H_2O$ | 22.3 |
| | $ZnSO_4 7H_2O$ | 8.6 |
| | $CuSO_4 5H_2O$ | 0.025 |
| | $CaCl_2 2H_2O$ | 332 |
| | KI | 0.83 |
| | $CoCl_2 6H_2O$ | 0.025 |
| | $KH_2PO_4$ | 170 |
| | $H_3BO_3$ | 6.2 |
| | $Na_2MoO_4 2H_2O$ | 0.25 |
| | FeNaEDTA | 36.7 |
| Vitamin | Myo-inositol | 100 |
| | Thiamine-HCl | 0.1 |
| | Nicotinic acid | 0.5 |
| | Pyridoxine-HCl | 0.5 |
| Amino acid | Glycine | 2 |
| Hormone | 2,4-D | 1 |
| Sucrose | | 30,000 |

Meanwhile, ginseng cotyledon-derived callus (KCTC 10224) was purchased from the Biological Resource Center (Korea) and subcultured at intervals of 3 weeks.

2-2: Preparation of Carrot Cambial Meristematic Cells (CMCs)

A carrot plant (*Daucus carota* L.) was prepared and surface-sterilized in the same manner as described in Example 2-1. Next, the prepared sample was treated with stress in the same manner as described in Example 2-1, followed by induction of cambial cells in the sample.

As a result, it was shown that tissues other than the cambium were necrotized, and cambial meristematic cells (CMCs) having the ability to divide were induced, like the results of Example 2-1. A carrot cambium-containing explant was proliferated in the same manner as described in Example 2-1.

Meanwhile, to culture carrot callus as a control, the carrot root was collected and surface-sterilized in the same manner as described in Example 2-1, and then an explant was prepared from the carrot root. The prepared explant was placed on the callus induction medium shown in Table 10 below and was cultured in a dark room controlled to 21±1° C. Amorphous callus was harvested, and then subcultured at intervals of 14 days.

TABLE 10

Callus induction medium (medium 8)

| | Composition | Contents(mg/L) |
|---|---|---|
| Inorganic salts | $KNO_3$ | 1900 |
| | $(NH_4)_2SO_4$ | 1650 |
| | $MgSO_4 7H_2O$ | 180.54 |
| | $MnSO_4 4H_2O$ | 22.3 |
| | $ZnSO_4 7H_2O$ | 8.6 |
| | $CuSO_4 5H_2O$ | 0.025 |
| | $CaCl_2 2H_2O$ | 332 |
| | KI | 0.83 |
| | $CoCl_2 6H_2O$ | 0.025 |
| | $KH_2PO_4$ | 170 |
| | $H_3BO_3$ | 6.2 |
| | $Na_2MoO_4 2H_2O$ | 0.25 |
| | FeNaEDTA | 36.7 |
| Vitamin | Myo-inositol | 100 |
| | Thiamine-HCl | 0.1 |
| | Nicotinic acid | 0.5 |
| | Pyridoxine-HCl | 0.5 |
| Amino acid | Glycine | 2 |
| Hormone | 2,4-D | 2 |
| Sucrose | | 30,000 |
| Gelrite | | 3,000 |

2-3: Proliferation and Characterization of Cambial Meristematic Cells (CMCs) from Storage Root The wild ginseng cambial meristematic cells (CMCs) isolated in Example 1 above were placed in a flask containing the liquid medium shown in Table 2 below. Then, the cells in the flask were cultured in a rotating shaker under dark conditions at 100 rpm at 21±1° C. For continuous culture, the wild ginseng cambial meristematic cells (CMCs) cultured for proliferation were suspension-cultured at a cell-to-medium volume ratio of 1:10 for 14 days. In addition, the wild ginseng callus isolated in Example 2-1 was also cultured under the same conditions, and the liquid medium used for culture of the callus was the same as the liquid medium used for culture of the wild ginseng cambial meristematic cells (CMCs).

The degree of aggregation of the cells was observed with biological microscope CX31 (Olympus, Japan). As a result, as shown in A of FIG. 2, it could be seen that the cambial meristematic cells (CMCs) according to the present invention included a large number of single cells during suspension culture, and some of the cells were present as cell aggregates having a very small size. Specifically, when the cambial meristematic cells (CMCs) according to the present invention were cultured, the maximum size of the cell aggregates was only 200 μm. On the contrary, when the control was observed, the callus cells were highly aggregated as shown in B of FIG. 2, and the maximum size of the cell aggregates was 500 μm. In addition, the cambial meristematic cells (CMCs) according to the present invention and the cells of the callus were sampled after proliferative culture, but before subculture, and the cell viability (%) of the samples were calculated using a 2% Evan's blue staining (5 min) method. As a result, the cambial meristematic cells (CMCs) according to the present invention showed a viability of 94.3%, whereas the callus cells showed a viability of only 61%.

Meanwhile, the carrot cambial meristematic cells (CMCs) isolated in Example 2-2 above were placed in a flask containing the liquid medium (medium 3-1). Then, the cells in the flask were cultured in a rotating shaker under dark conditions at 100 rpm at 25±1° C. For continuous culture, the carrot cambial meristematic cells (CMCs) cultured for proliferation were suspension-cultured at a cell-to-medium volume ratio of 1:10 for 14 days. In addition, the carrot callus isolated in Example 2-2 was also cultured under the same conditions, and the liquid medium used for culture of the callus was the same as the liquid medium used for culture of the carrot cambial meristematic cells (CMCs).

Example 3

Preparation of Expression Vector for Transformation of Plant Cambial Meristematic Cells (CMCs) and Culture of *Agrobacteria*

An experiment was performed in the following manner using a plant expression binary vector containing GFP gene and *Agrobacterium tumefaciens* LBA4404 purchased from Takara Korea Biomedical (LBA4404 Electro cells, cat no. 9115, Korea).

The introduction of the purchased GFP-containing binary vector into *agrobacteria* was performed using Bio-Rad Cuvette and Gene Pulser II according to the instructions of the manufacturer (for *Agrobacterium tumefaciens* LBA4404).

The prepared pBINmGFP5ER/LBA4404 was inoculated with a platinum pool in 15% glycerol stock and streaked on YEP solid medium (medium 9) supplemented with 100 mg/L rifampicin (TCI, Japan) and 100 mg/L kanamycin, followed by culture at 28° C. for 3 days under dark conditions.

TABLE 11

YEP solid medium for culture of Agrobacteria (medium 9)

| Components | Contents |
| --- | --- |
| Peptone | 10 g |
| Yeast Extract | 10 g |
| NaCl | 5 g |
| Agar | 15 g |
| Kanamycin | 100 mg/L |
| Rifampicin | 100 mg/L |
| total volume | 1000.0 ml |

The *Agrobacteria* (pBINmGFP5ER/LBA4404) were streaked on fresh medium at intervals of 3 days and subcultured at 28° C. under dark conditions.

The *Agrobacteria* were suspension-cultured to transform plant cambial meristematic cells (CMCs) by the *Agrobacteria*.

A single colony of the *Agrobacteria* cultured on the solid medium was added to 5 ml of YEP liquid medium (Table 12; medium 10) and cultured at 28° C. and 200 rpm for 6-18 hours under dark conditions, after which 1-5 ml of the *Agrobacteria* culture was added to 100 ml of YEP medium and cultured at 28° C. and 200 rpm for 6-24 hours.

TABLE 12

YEP liquid medium (medium 10) for culture of Agrobacteria

| Components | Contents |
| --- | --- |
| Peptone | 10 g |
| Yeast Extract | 10 g |
| NaCl | 5 g |
| Kanamycin | 100 mg/L |
| Rifampicin | 100 mg/L |
| total volume | 1000.0 ml |

1 ml of each of the prepared *Agrobacteria* suspension and an YEP liquid medium (containing 100 mg/L rifampicin and 100 mg/L kanamycin) to be used as a control was sampled by a pipette and placed in a cuvette, and the optical density ($OD_{600}$) at a wavelength of 600 nm was measured using a UV/visible spectrophotometer. The UV spectrophotometer used was the product of Amersham Bioscience.

For virulence induction of the *Agrobacteria*, the *Agrobacteria* suspension having an $OD_{600}$ value of 0.4-2.0 was placed in a conical tube (BD FALCON, USA) and centrifuged (Hanil Science Industrial Co., Ltd., Korea) at 4° C. and 6000 g-force for 3-10 minutes. The *Agrobacteria* pellets present on the tube wall were collected and resuspended in 10 mL of suspension medium (medium 2). When the $OD_{600}$ value of the *Agrobacteria* reached 0.00001-2.0, 10-200 µM of acetosyringone (Aldrich, USA) was added to the *Agrobacteria* suspension which was then incubated with shaking at 28° C. and 200 rpm for 1 minute to 24 hours.

The *Agrobacteria* may be treated with acetosyringone as described in the present invention, or plant cambial meristematic cells (CMCs) may be treated directly with acetosyringone. Alternatively, the *Agrobacteria* and plant cambial meristematic cells (CMCs) may be simultaneously treated with acetosyringone.

Example 4

Transient Expression of Target Protein in Plant Cambial Meristematic Cells (CMCs) by Plant Transformation Vector For transformation of plant cambial meristematic cells (CMCs), *Agrobacteria* were prepared as described in Example 3 above. The exponential growth phase cells of Examples 1 and 2 were prepared as cambial meristematic cells (CMCs) and cultured at a cell-to-medium volume ratio of 1:10.

10 mL of virulence-induced *Agrobacteria* suspension was placed in a 250 ml flask containing the tomato cambial meristematic cells (CMCs) isolated in Example 1 and was co-cultured with the cells at 25° C. and 100 rpm. In order to maximize the transformation efficiency of the tomato CMCs in this process, the culture was cultured in a rotating shaker (Sejong, Korea) at 100 rpm for 1 minute to 48 hours under dark conditions, and then settled for 1 minute to 48 hours without shaking. Next, the culture was cultured again in a rotating shaker at 100 rpm for 1-9 days.

1 mL of the culture co-cultured for 1-9 days was sampled by a pipette and placed in a 1.5 ml microtube. 10 µL of the 1 mL sample was loaded into a hemacytometer (Marienfeld), and the expression of GFP therein was observed using an IX71 Inverted microscope (fluorescence light source: U-RFL-T). In the observation, green light and a wavelength of 460-490/520 nm (excitation/barrier) were used. The percentage of GFP-expressed cells relative to living cells on the same slide was counted using an optical microscope.

Figure 4:
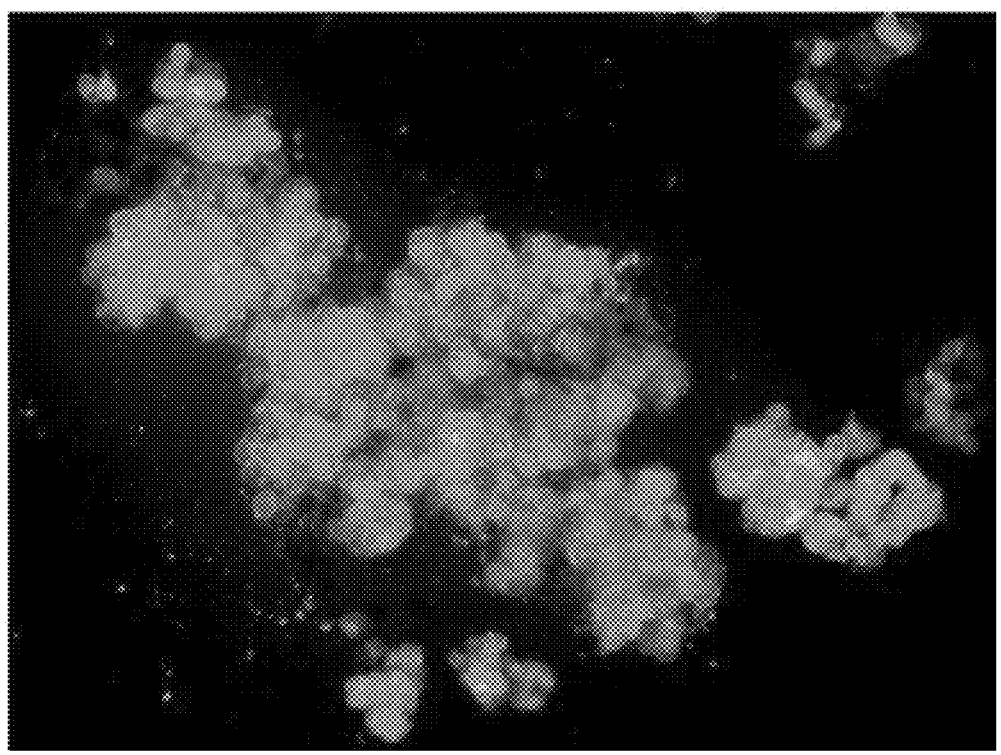
FIG. 4 is a photograph showing the transient expression of green fluorescent protein (GFP), which indicates that an 90% or more of tomato cambial meristematic cells (CMCs) was infected with Agrobacteriua after 5 days of co-culture.

GFP was transiently expressed in the tomato cambial meristematic cells (CMCs) by the *Agrobacteria*, and as a result, as can be seen in FIG. 4, GFP was transiently expressed in 90% of the living cells by the *Agrobacteria* at 1-9 days of co-culture, and most preferably after 5 days of co-culture. It was shown that, during the co-culture period, the tomato cambial meristematic cells (CMCs) showed a decrease in viability of less than 10%, and the rigidity of the cell wall was maintained intact.

In other words, it is known that transformation at the cell culture level is difficult such that it cannot be calculated in terms of percentage, but it could be seen that the application of the tomato cambial meristematic cells (CMCs) according to the present invention showed a significant transformation efficiency of 90% or higher.

Meanwhile, the tomato callus was co-cultured under the same conditions as described above, and as a result, the tomato callus of Example 1 showed a low transformation efficiency of 26.4%, unlike the tomato cambial meristematic cells (CMCs) according to the present invention. However, this value was at least two times higher than 10% which the previously reported callus transformation efficiency.

TABLE 13

Results of transient expression of GFP in transformed cambial meristematic cells and callus

|  | Tomato cambial meristematic cells | Tomato callus |
|---|---|---|
| Co-culture period | 4-9 days | 6-9 days |
| Viability | 91.8% | 64.7% |
| GFP expression level | 88.7% (97% relative to viability) at day 5 | 26.4% at day 7 |

Figure 7:
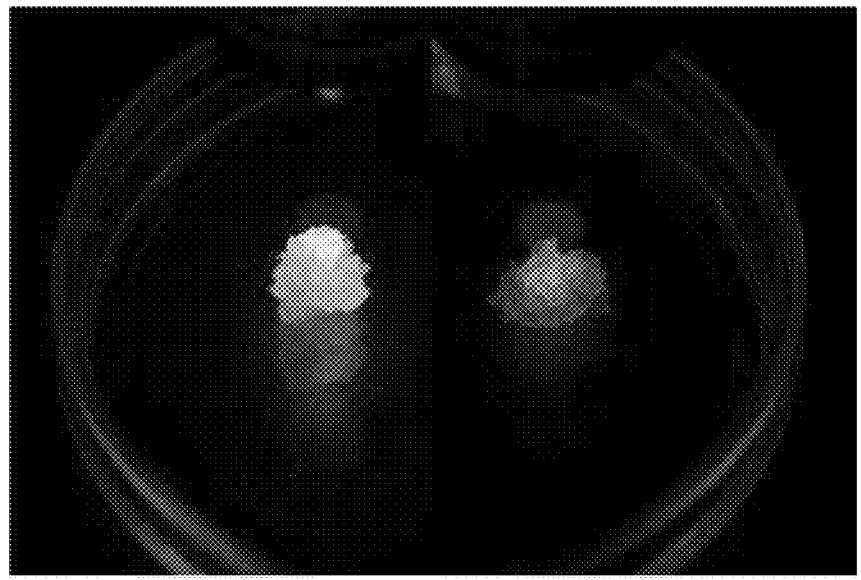
FIG. 7 is a photograph showing the results of observing a clump, which expresses GFP as a result of stable transformation into tomato cambial meristematic cells (CMCs), and a non-transformed clump, under UV light.
Figure 8:
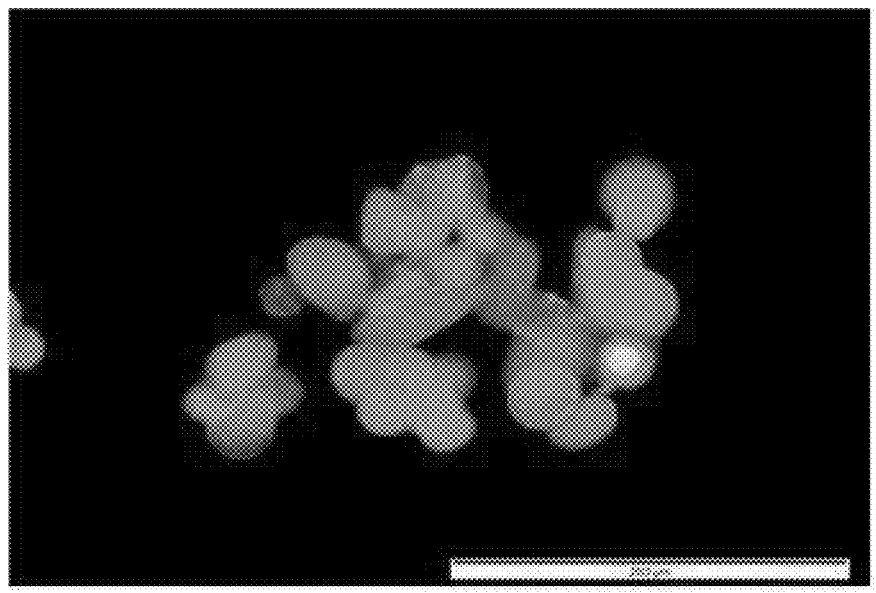
FIG. 8 is a fluorescence micrograph for tomato cambial meristematic cells (CMCs) with stably transformed GFP.

In addition, for the wild ginseng and carrot cambial meristematic cells (CMCs) of Example 2, an experiment was performed in the same manner as described above, and the results of the experiment are shown in FIGS. 7 and 8.

Figure 5:
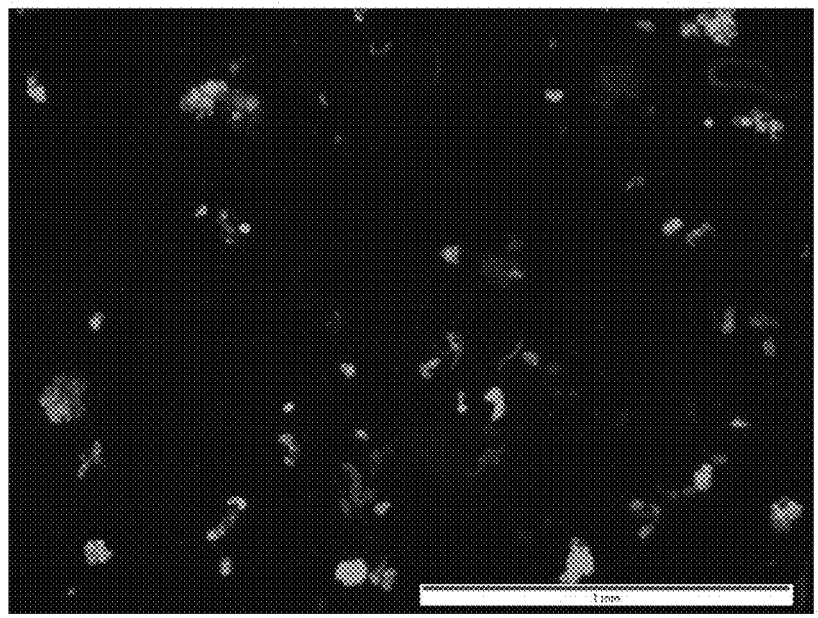
FIG. 5 is a photograph showing the transient expression of GFP in wild ginseng cambial meristematic cells (CMCs) after 10 days of co-culture with *Agrobacteriua* .

Referring to FIG. 5, it could be seen that, when the wild ginseng cambial meristematic cells (CMCs) were transiently co-cultured with the *Agrobacteria*, 13% or more of the living cells were infected with the *Agrobacteria* and expressed GFP.

Figure 6:
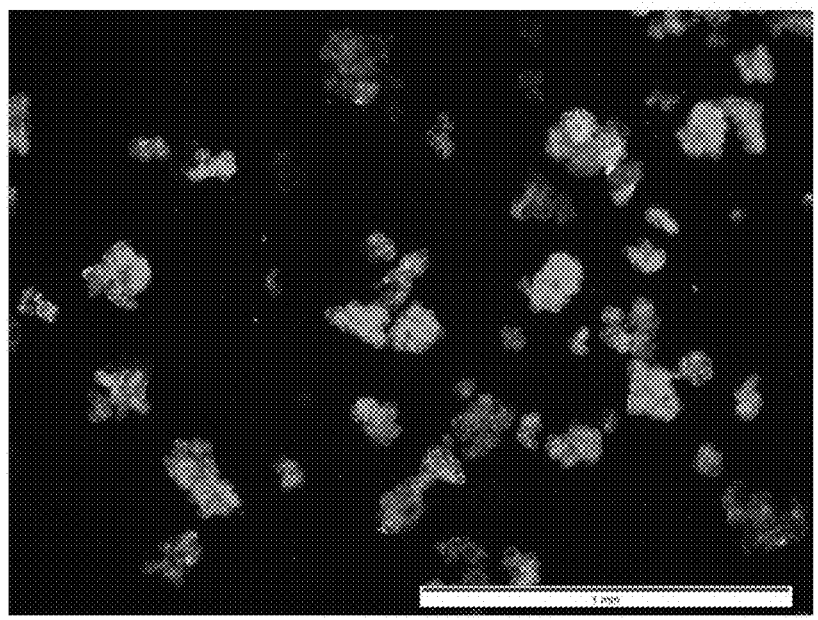
FIG. 6 is a photograph showing the transient expression of GFP in carrot cambial meristematic cells (CMCs) after 10 days of co-culture with *Agrobacteriua* .

Referring to FIG. 6, it could be seen that, when the carrot cambial meristematic cells (CMCs) were transiently co-cultured with the *Agrobacteria*, 17% or more of the living cells were infected with the *Agrobacteria* and expressed GFP. The transient expression levels of GFP in the wild ginseng and carrot cambial meristematic cells (CMCs) were lower than that in the tomato cambial meristematic cells (CMCs), but it is expected that the wild ginseng and carrot cambial meristematic cells (CMCs) can show transient expression levels comparable to that in the tomato cambial meristematic cells when the co-culture time and the static culture time are controlled.

Example 5

Examination of Stable Transformation of Target Protein into Plant Cambial Meristematic Cells (CMCs) by Plant Expression Vector After the procedure described in Example 4 was performed, the tomato cambial meristematic cells (CMCs) were co-cultured with the *Agrobacteria* in a 250 ml flask at 25° C. and 100 rpm for 3-21 days. At a time point when the expression of GFP was the highest, the culture was washed with the suspension medium (medium 3) shown in Table 2 for 5-20 minutes to remove the *Agrobacteria*. Next, the culture was treated with 300 mg/l of kanamycin (TCI, Japan) and 500 mg/l of cefotaxime (TCI, Japan) and suspension-cultured with shaking at 25° C. and 100 rpm for 1 week. Subsequently, the cambial meristematic cells (CMCs) were precipitated, and the largest possible amount of the medium was removed by decantation, after which the remaining medium was mostly absorbed with filter paper (70 mm, Toyo Roshi Kaisha, Japan), and the tomato cambial meristematic cells (CMCs) were placed on solid selection medium (Table 14; medium 11). The placed cells were cultured at 25±1° C. under dark conditions, thereby obtaining transgenic cambial meristematic cells (TCMCs) that express GFP. The carrot cambial meristematic cells (CMCs) were treated in the same manner as described above, and the wild ginseng cambial meristematic cells (CMCs) were plated on a medium obtained by excluding the hormone from medium 11.

TABLE 11

Solid selective medium (medium 11) for CMCs

|  | Composition | Contents(mg/L) |
|---|---|---|
| Inorganic salts | $Ca(NO_3)_2$ | 471.26 |
|  | $NH_4NO_3$ | 400 |
|  | $MgSO_4 7H_2O$ | 180.54 |
|  | $MnSO_4 4H_2O$ | 22.3 |
|  | $ZnSO_4 7H_2O$ | 8.6 |
|  | $CuSO_4 5H_2O$ | 0.25 |
|  | $CaCl_2 2H_2O$ | 72.5 |
|  | $K_2SO_4$ | 990 |
|  | $Na_2MoO_4 2H_2O$ | 0.25 |
|  | $H_3BO_3$ | 6.2 |
|  | $KH_2PO_4$ | 170 |
|  | FeNaEDTA | 36.7 |
| Vitamin | Myo-inositol | 200 |
|  | Thiamine-HCl | 20 |
|  | Nicotinic acid | 2 |
|  | Pyridoxine-HCl | 2 |
|  | L-ascorbic acid | 50 |
|  | Citric acid | 75 |
| Amino acid | L-aspartic acid | 133 |
|  | L-arginine | 175 |
|  | Glycine | 75 |
|  | Proline | 115 |
| Hormone | 2,4-D (Dichlorophenoxyacetic acid) | 1 |
| Sucrose |  | 30,000 |
| Kanamycin |  | 300 |
| Cefotaxime |  | 300 |
| Gelrite |  | 3,000 |

The obtained cell line was observed under UV light, and as a result, the stably transformed cell line emitted GFP fluorescence as shown in the left clump of FIG. 7, whereas the non-transformed cell line did not emit GFP fluorescence as shown in the right clump. To examine green fluorescence emission from each cell line in the clumps, the degree of fluorescence emission was analyzed using a fluorescence microscope (Olympus IX71 inverted microscope; fluorescence light source: U-RFL-T).

As a result, as shown in FIG. 8, GFP was expressed in all the sample cells, indicating that stable transformation of the plant cambial meristematic cells (CMCs) according to the present invention was successful.

Figure 9:
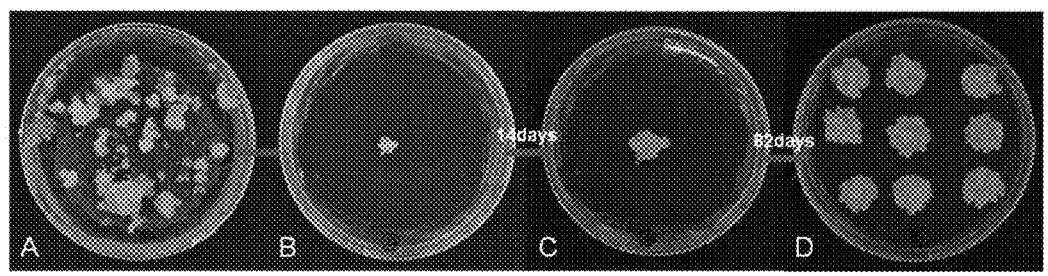
FIG. 9 is a set of photographs showing the results of proliferating GFP-expressing cells by continuously subculturing selected clusters, which were confirmed to emit fluorescence.

In addition, clusters confirmed to emit fluorescence as described above were selected (A of FIG. 9) and subcultured, and the expression of GFP therein was analyzed (B of FIG. 9). Next, the clusters were subcultured for proliferation at intervals of 14 days (C of FIG. 9: after 14 days; D of FIG. 9: after 82 days of continuous subculture), and it could be seen that the clusters stably expressed GFP.

This suggests that transgenic cambial meristematic cells (TCMCs) confirmed to be stably transformed can be continuously proliferated by subculture. It is to be noted that the transgenic cambial meristematic cells (TCMCs) transformed with GFP showed very strong green fluorescence. This quantitatively indicates that GFP was strongly expressed in the plant cambial meristematic cells (CMCs). Not only the overall expression level of GFP, but also the yield at which individual cells express the protein, influences the overall yield. Thus, the degree of expression of green fluorescence suggests that a target protein can be expressed at a very high level in the transgenic cambial meristematic cells (TCMCs).

In addition, the results of stable transformation into the tomato, carrot and wild ginseng cambial meristematic cells were compared between the case in which the sedimentation was performed and the case in which the sedimentation was not performed. In addition, the results for cambial meristematic cells (CMCs) were compared with the results for callus.

Figure 10:
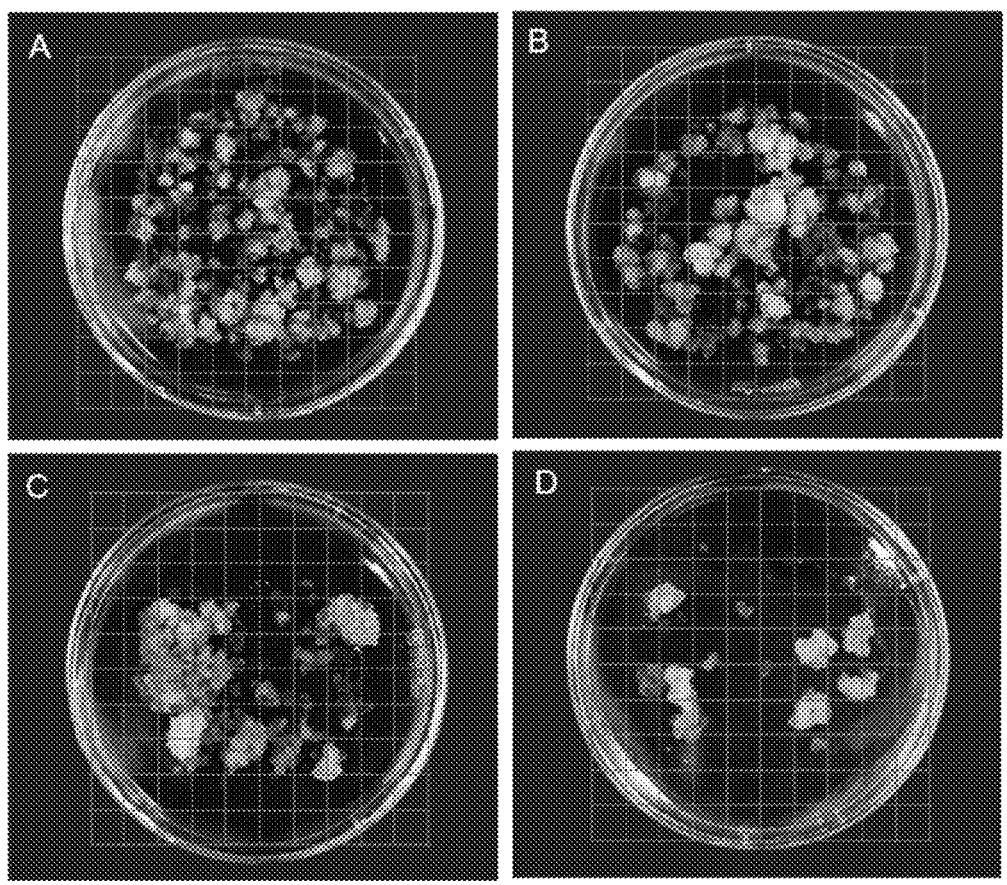
FIG. 10 is a set of photographs showing a comparison of stable transformation into tomato cambial meristematic cells (CMCs) or callus between the case in which the sedimentation was performed and the case in which the sedimentation was not performed.

As a result, as can be seen ion FIG. 10, the number of clusters formed was larger in tomato cambial meristematic cells (TCMCs; A of FIG. 10) or tomato callus (C of FIG. 10), which were subjected to the sedimentation, than in tomato cambial meristematic cells (TCMCs; B of FIG. 10) or tomato callus (D of FIG. 10) which were not subjected to the sedimentation. In addition, the number of clusters formed was larger in tomato cambial meristematic cells (TCMCs; A and B of FIG. 10) than in tomato callus (C and D of FIG. 10).

Figure 11:
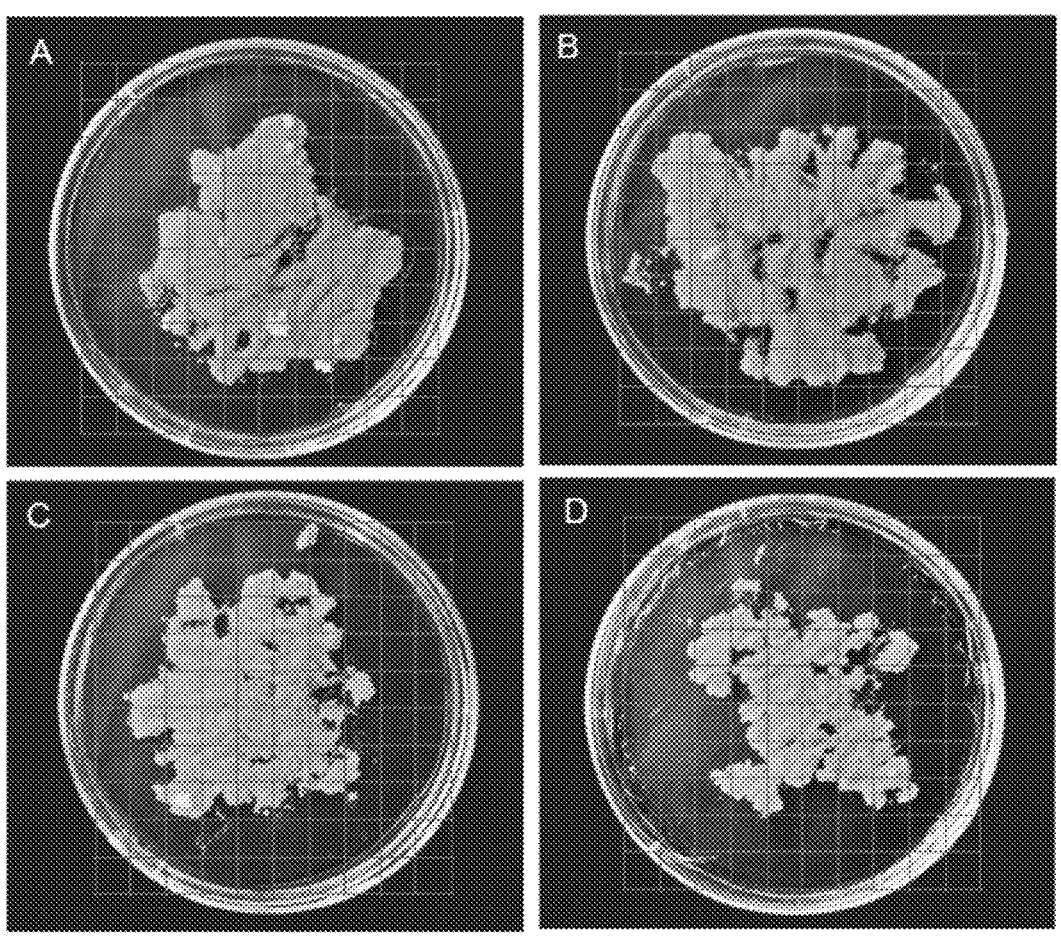
FIG. 11 is a set of photographs showing a comparison of stable transformation into carrot cambial meristematic cells (CMCs) or callus between the case in which the sedimentation was performed and the case in which the sedimentation was not performed.

As shown in FIG. 11, the number of formed clusters (indicated portions in A and B of FIG. 13) was larger in carrot cambial meristematic cells (TCMCs; A of FIG. 11) or carrot callus (C of FIG. 11), which were subjected to the sedimentation, than in carrot cambial meristematic cells (TCMCs; B of FIG. 11) or carrot callus (D of FIG. 11) which were not subjected to the sedimentation. In addition, the number of clusters formed was larger in carrot cambial meristematic cells (TCMCs; A and B of FIG. 11) than in carrot callus (C and D of FIG. 11).

Figure 12:
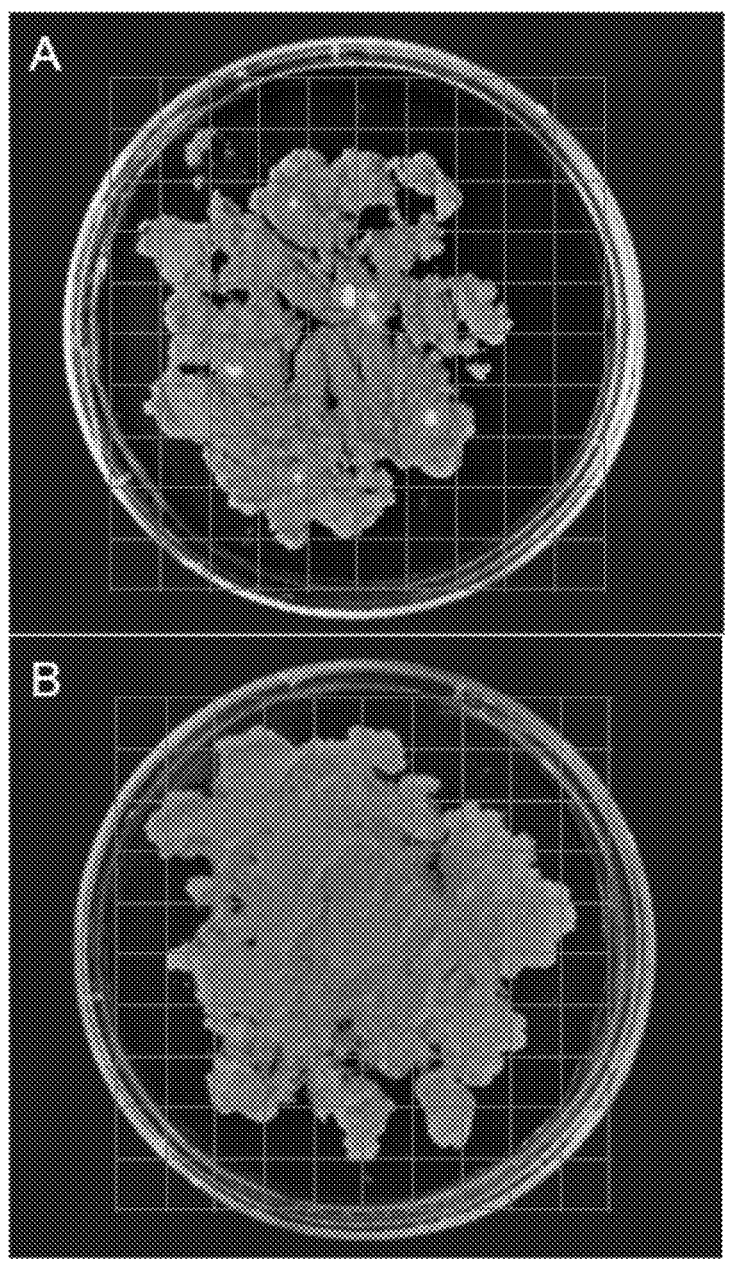
FIG. 12 is a set of photographs showing a comparison of stable transformation into wild ginseng cambial meristematic cells (CMCs) between the case in which the sedimentation was performed and the case in which the sedimentation was not performed.

As shown in FIG. 12, the number of clusters formed was larger in wild ginseng cambial meristematic cells (TCMCs; A of FIG. 12), which were subjected to the sedimentation, than in wild ginseng cambial meristematic cells (TCMCs; B of FIG. 12).

The formation of clusters means that the T-DNA of agrobacteria was inserted into the genome of plant cells. From the results in FIGS. 10 to 12, it can be seen that the sedimentation is an important factor in increasing the efficiency of transformation.

In addition, it was observed that the number of clusters formed was larger in transgenic cambial meristematic cells (TCMCs) than in callus under the same conditions, suggesting that the use of cambial meristematic cells (TCMCs) as a material is an important factor in increasing the efficiency of transformation.

Example 6

Examination of Possibility of Scale-up Culture 70 ml of cells, settled in a 250 mL flask and confirmed to show a GFP expression level of 90% or higher in Example 4, were seeded in a 3 L air-lift bioreactor at a cell-to-medium ratio of 1:30. The dry cell weight was 0.6 g/L. The working volume of the 3-L bioreactor was 2,100 ml, and the volume utilization of the bioreactor was 70% of the total volume. The medium used was the same as the medium used in the 250-mL flask. An antibiotic was added, after which the cells were cultured at an aeration rate of 0.1-0.15 vvm (volume/volume/minute) at 25° C.±1 for 7-10 days under dark conditions. Subculture in the 3-L bioreactor was performed at intervals of 7-10 days, and preferably 7 days.

Figure 13:
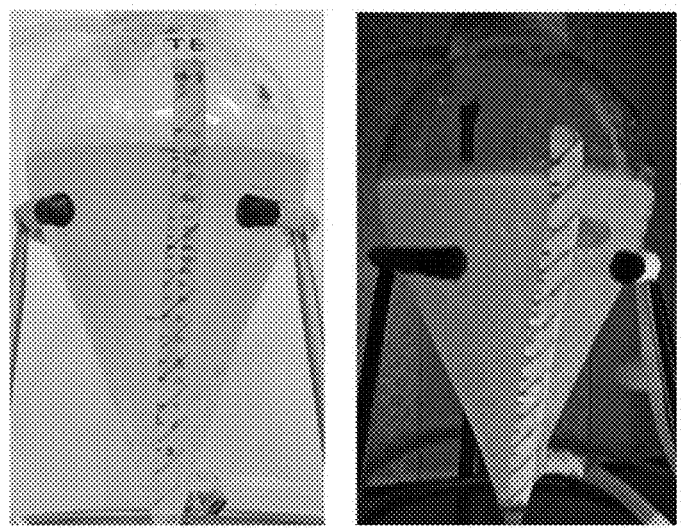
FIG. 13 is a photograph showing the results of the expression of GFP after culturing transgenic GFP tomato cambial meristematic cells (TCMCs) in a 3 L bioreactor, irradiating the cells with UV light.

The transgenic tomato cambial meristematic cells (TCMCs) were cultured in the 3-L bioreactor. As a result, as shown in FIG. 13, the same GFP expression level as that in the 250 ml flask culture could be seen when the cells were irradiated with UV light (350 nm) at 7-10 days of proliferative culture. The growth rate of the transformed tomato cambial meristematic cells (TCMCs) was at least 10-fold higher after completion of proliferative culture compared to the amount of cells seeded in the initial stage. After completion of the proliferative culture, the transgenic tomato cambial meristematic cells (TCMCs) showed a decrease in viability of less than 10%, and the results of observation with an optical microscope indicated that the rigidity of the cell wall was maintained without changes.

TABLE 15

Results of culture of tomato cambial meristematic cells expressing GFP in 3 L bioreactor

| | Tomato cambial meristematic cells |
|---|---|
| Proliferative culture period | 7-10 days |
| Viability | 85% |
| Growth rate (folds) | >10 folds |
| GFP expression level | 85% (100% relative to viability) at day 7 |

Example 7

Construction of Transgenic Tobacco Plant 7-1: Culture of *Agrobacteria*

*Agrobacteria* of a pBINmGFP5ER/LBA4404 single colony was added to 5 ml of YEP medium and cultured at 28° C. for 6 hours. Next, the culture was added to 50 ml of YEP medium at a ratio of 1:50-1:100 and cultured for 18 hours within a total of 24 hours, and then the OD of the *Agrobacteria* culture was measured. The *Agrobacteria* culture was placed in a conical tube, and the cells were spun down using a centrifuge at 4° C. Tobacco culture medium (MS+2 mg/L BA+0.1 mg/L NAA+pH 5.8) was added to the collected *Agrobacteria* pellets, and based on the measured OD of the *Agrobacteria*, the tobacco culture medium was mixed with the *Agrobacteria* medium, and 10-200 μM acetosyringone was added thereto, followed by culture at 250 rpm at 28° C. for 2 hours.

7-2: Preparation of Tobacco Leaf Explants

Leaves were detached while holding the petioles of the plant with tweezers and placed in a Petri dish. A 1.0 cm×1.0 cm (~0.5 cm×0.5 cm) explant including a main vein portion close to the petiole was made using a knife.

7-3: Co-culture

A positive control (PC) explant was separated, placed on co-culture medium (MS+2 mg/L BA+0.1 mg/L NAA+pH 5.8+0.8% agar), and then cultured at 25° C. for 7 days under dark conditions. The explant (excluding the positive control) prepared in Example 7-2 was added to the cultured prepared in Example 7-1, after it was immersed for 20 minutes while it was mildly shaken at intervals of 5 minutes, thereby agro-inoculating the explant. The explant was taken out and placed on filter paper to remove moisture, and then the explant was placed on co-culture medium (MS+2 mg/L BA+0.1 mg/L NAA+pH 5.8+0.8% agar+100 μM AS) and cultured at 25° C. for 3 days under dark conditions.

7-4: Selection

The co-cultured explant was washed three times with sterile water and dried with filter paper. An explant to be used as a negative control (NC) was separated from PC. PC was placed on regeneration medium (MS+2 mg/L BA+0.1 mg/L NAA+pH 5.8+0.8% agar), NC was placed on selection medium (MS+2 mg/L BA+0.1 mg/L NAA+pH 5.8+0.8% agar medium+kan 100 mg/L+cef 500 mg/L), and the remaining explant was placed on selection medium.

Figure 14:
FIG. 14 is a photograph showing the results of acclimating transgenic *Nicotiana benthamiana* and growing the acclimated plant in a flowerpot.

After culture for 3 weeks under dark conditions, each of the explants was cultured with 16-hr light/8-hr dark cycles to form shoots. When the shoots were formed, only one shoot was picked and transferred to root formation medium (MS+kan 100 mg/L+cef 500 mg/L pH 5.8+0.8% agar) to form roots. FIG. 14 shows the results of acclimating transgenic *N. benthamiana* and growing the acclimated plant in a flowerpot.

Figure 15:
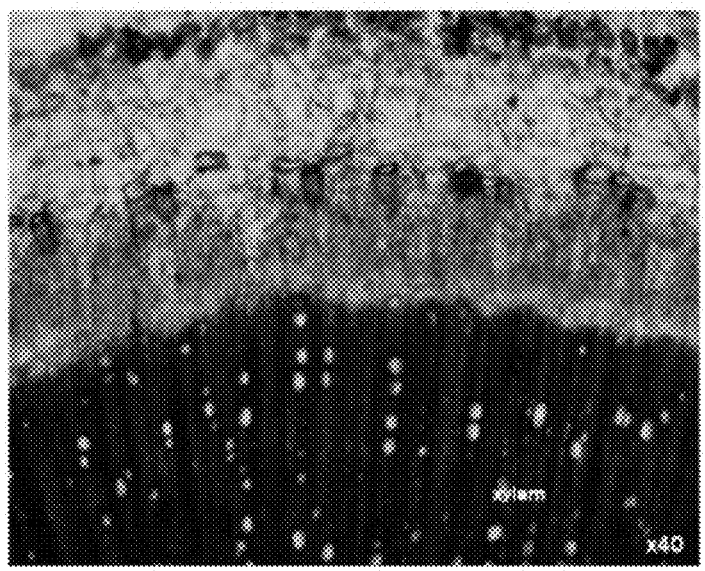
FIG. 15 is a photograph showing the results of observing the morphology of a collected tobacco stem.

7-5: Observation of Morphology 3-6-month-old stems were collected and the morphology thereof was observed. For observation, the stems were cross-sectioned and radially sectioned, and for tissue discrimination, the stems were observed by staining with the xylem-specific dye reagent phloroglucinol-HCl. As can be seen in FIG. 15, the xylem was stained red, and 2-4 cambial layers (3-6 cambial layers for *Nicotiana tabacum* cv. *Xanthi*) were present immediately above the xylem.

Figure 16:
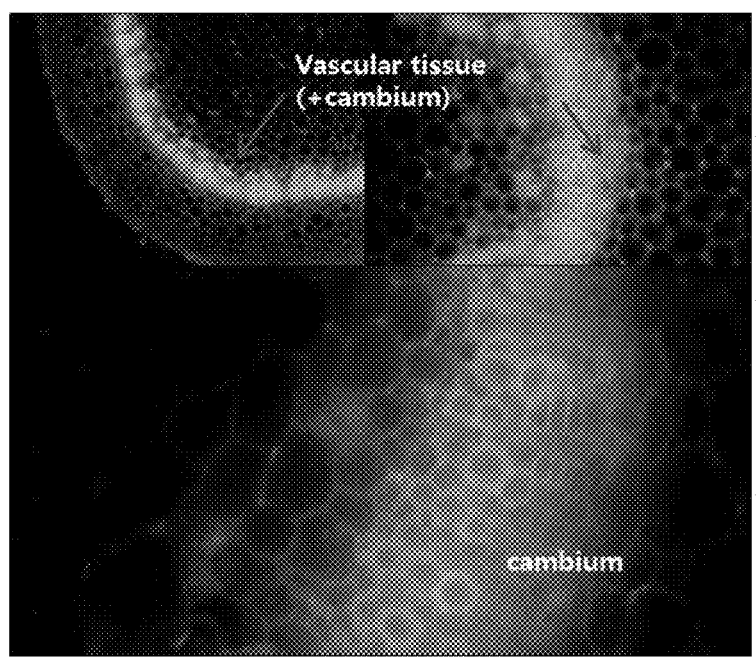
FIG. 16 is a photograph showing the results of cross-sectioning and observing a tobacco plant transformed with GFP.

In addition, the tobacco plant transformed with GFP was cross-sectioned and observed using a GFP filter (excitation/barrier: 460-490/520 nm). As a result, as shown in FIG. 16, fluorescence was more intense in the cambial zone than in other tissues.

7-6: Separation of Transgenic Cambial Meristematic Cells (TCMC) of Tobacco

Figure 17:
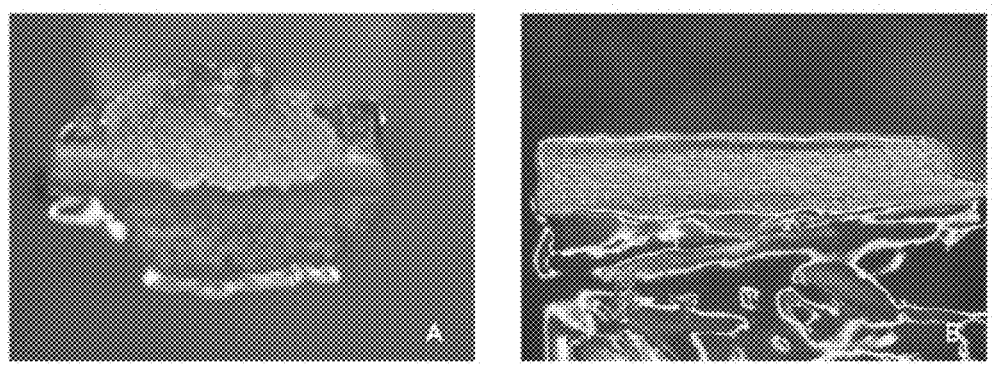
FIG. 17 is a photograph showing the results of isolating transformed cambial meristematic cells (TCMCs) from the cambial zone of transgenic *Nicotiana benthamiana.*
Figure 18:
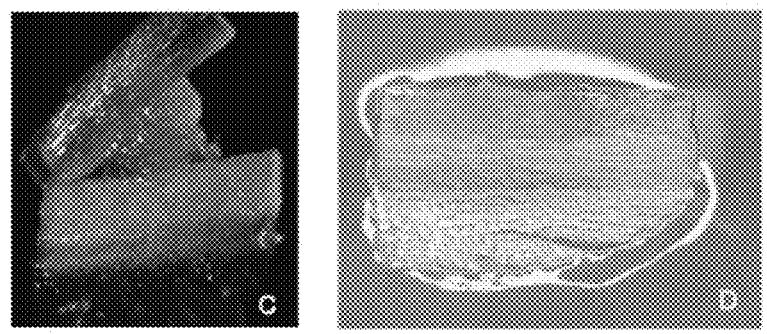
FIG. 18 is a photograph showing the results of isolating cambial meristematic cells (TCMCs) from the cambial zone of transgenic *Nicotiana tabacum* cv. *xanthi.*

At 4 days of culture, cell division was observed in the cambial zone of *N. benthamiana*. After 2 weeks of culture, as shown in FIG. 17(A), the phloem tissue other than the cambium was detached with tweezers. As shown in FIG. 17(B), the cell division or injury of other tissues other than the phloem after separation was not observed. In the case of *Nicotiana tabacum* cv. *Xanthi*, cambial meristematic cells were separated in the same manner as described for *N. benthamiana*, and as shown in FIG. 18, the same results were also obtained for *Nicotiana tabacum* cv. *Xanthi*.

7-7: Analysis of Expression of Protein in Tobacco Cambial Meristematic Cells (TCMCs) and Tobacco Plant A total soluble protein was isolated from each of the tobacco cambial meristematic cells (TCMCs) and tobacco plant transformed with GFP gene and a non-transformed tobacco plant.

The isolated total soluble proteins were subjected to SDS-PAGE on two polyacrylamide gels and transferred to nitrocellulose paper using a semi-dry transfer cell (BIO-RAD).

The paper was blocked overnight with 5% skim milk and washed with TBST, after which it was reacted sequentially with anti-GFP primary antibody and secondary antibody. Next, it was washed with TBST/TNM and developed with a developer (BCIP/NBT sol.), after which protein bands were analyzed.

Figure 19:
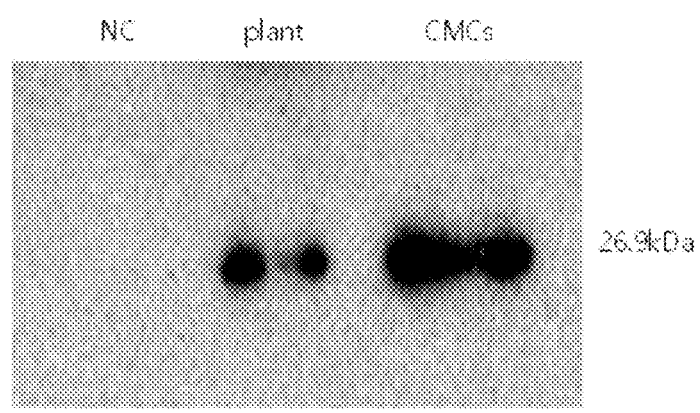
FIG. 19 is a photograph showing the results of Western blot analysis on a total soluble protein extracted from both transgenic GFP plant and cambial meristematic cells (TCMCs) isolated from the plant.

As a result, as shown in FIG. 19, no band was detected in the non-transgenic tobacco plant. In the transgenic tobacco plant and the tobacco cambial meristematic cells (TCMCs) isolated from the transgenic tobacco plant, a band was detected at a location similar to the GFP size.

In addition, it could be seen that the GFP protein was more highly expressed in the tobacco cambial meristematic cells (TCMCs) isolated from the transgenic tobacco plant than in the transgenic tobacco plant. Such results are consistent with the results of FIG. 16 that indicate that the results for the tobacco cambial meristematic cells (TCMCs) were higher.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

INDUSTRIAL APPLICABILITY

As described above, the system of expressing a target protein using the recombinant plant cells according to the present invention can overcome the problems of conventional plant cell culture. In addition, it shows significantly high transformation efficiency, and thus can produce high level of target proteins, including biopharmaceutical proteins. Accordingly, it enables the commercialization of biopharmaceutical drugs, including protein products of plant origin.

The invention claimed is:

1. A method of producing a protein, comprising:
   mixing, in a culture, tomato cambial meristematic cells (CMCs) and *Agrobacteria* that contain a vector comprising a gene encoding the protein, wherein the CMCs are a cell line containing innately undifferentiated cells and having meristematic continuity without going through dedifferentiation into callus;
   co-culturing the CMCs along with *Agrobacteria* containing the vector in the culture while shaking the culture for 1 minute to 48 hrs;
   subsequently co-culturing the CMCs and *Agrobacteria* containing the vector in the culture without shaking the culture, for sufficient time to sediment the CMCs in the culture to have a higher ratio of transfection of the gene encoding the protein than CMCs which are not sedimented;
   subsequently continuing to co-culture the CMCs and *Agrobacteria* containing the vector in the culture while shaking the culture;
   wherein said co-culturing of the CMCs and *Agrobacteria* containing the vector is carried out for a period of 1 to 9 days, and wherein during co-culturing of the CMCs and *Agrobacteria* containing the vector, the vector is introduced in the CMCs; and
   isolating the protein expressed in the culture.

2. The method of claim 1, wherein during co-culturing of the CMCs and *Agrobacteria* containing the vector, the gene encoding the protein is transfected in at least part of the CMCs so that the protein is transiently expressed in at least part of the CMCs.

3. The method of claim 1, wherein during co-culturing of the CMCs and *Agrobacteria* containing the vector, the gene encoding the protein is stably transformed into at least part of the CMCs.

4. The method of claim 1, further comprising co-culturing the CMCs and *Agrobacteria* containing the vector in the culture without shaking of the culture and with shaking of the culture such that co-culturing without shaking is intermittently performed between co-culturing with shaking.

5. The method of claim 1, wherein the culture containing *Agrobacteria* has an $OD_{600}$ not exceeding 2.0.

* * * * *